United States Patent [19]
Huntoon et al.

[11] Patent Number: 6,046,377
[45] Date of Patent: *Apr. 4, 2000

[54] ABSORBENT STRUCTURE COMPRISING SUPERABSORBENT, STAPLE FIBER, AND BINDER FIBER

[75] Inventors: Andrew Edsel Huntoon, Appleton, Wis.; Randy Emil Meirowitz, Roswell, Ga.; Sriram Padmanabhan Anjur; Robert John Phelan, both of Appleton, Wis.; Kim Te Tang, Neenah; Anthony John Wisneski, Kimberly, both of Wis.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/294,155

[22] Filed: Aug. 22, 1994

Related U.S. Application Data

[63] Continuation-in-part of application No. 08/157,802, Nov. 23, 1993, abandoned.

[51] Int. Cl.[7] ..................................................... A61F 13/15
[52] U.S. Cl. ........................... 604/368; 604/358; 604/367
[58] Field of Search ........................... 604/358, 365–368, 604/370, 372

[56] References Cited

U.S. PATENT DOCUMENTS

| | | |
|---|---|---|
| 4,426,417 | 1/1984 | Meitner et al. . |
| 4,429,001 | 1/1984 | Kolpin et al. . |
| 4,560,372 | 12/1985 | Pieniak .................................. 604/368 |
| 4,623,576 | 11/1986 | Lloyd et al. . |
| 4,650,479 | 3/1987 | Insley . |
| 4,655,757 | 4/1987 | McFarland et al. . |
| 4,724,114 | 2/1988 | McFarland et al. . |
| 4,773,903 | 9/1988 | Weisman et al. . |
| 4,865,596 | 9/1989 | Weisman et al. . |
| 4,879,170 | 11/1989 | Radwanski et al. . |
| 4,902,559 | 2/1990 | Eschwey et al. . |
| 4,923,454 | 5/1990 | Seymour et al. . |
| 4,931,355 | 6/1990 | Radwanski et al. . |
| 4,939,016 | 7/1990 | Radwanski et al. . |
| 4,950,531 | 8/1990 | Radwanski et al. . |
| 4,957,795 | 9/1990 | Riedel . |
| 4,988,560 | 1/1991 | Meyer et al. . |
| 5,013,309 | 5/1991 | Baigas, Jr. et al. . |
| 5,037,409 | 8/1991 | Chen et al. . |
| 5,135,787 | 8/1992 | Bair ........................................ 428/36.1 |
| 5,149,335 | 9/1992 | Kellenberger et al. . |
| 5,188,624 | 2/1993 | Young, Sr. et al. ................. 604/385.1 |
| 5,246,429 | 9/1993 | Poccia et al. . |
| 5,350,370 | 9/1994 | Jackson et al. .......................... 604/365 |
| 5,391,161 | 2/1995 | Hellgren et al. ......................... 604/368 |

FOREIGN PATENT DOCUMENTS

| | | |
|---|---|---|
| 0108637 | 5/1984 | European Pat. Off. . |
| 0156160 | 10/1985 | European Pat. Off. . |
| 0156649 | 10/1985 | European Pat. Off. . |
| 0175481 | 3/1986 | European Pat. Off. . |
| 0306262A1 | 3/1989 | European Pat. Off. . |
| 0443627 | 8/1991 | European Pat. Off. . |
| 0615736 | 9/1994 | European Pat. Off. . |
| 0633009A2 | 1/1995 | European Pat. Off. . |
| 2214201 | 8/1989 | United Kingdom . |
| 2263914 | 8/1993 | United Kingdom . |
| 2266465 | 11/1993 | United Kingdom . |

Primary Examiner—John G. Weiss
Assistant Examiner—Dennis Ruhl
Attorney, Agent, or Firm—Sebastian C. Pugliese, III

[57] ABSTRACT

Disclosed is an absorbent structure containing superabsorbent material, wettable staple fiber, and wettable binder fiber. The absorbent structure exhibits a liquid uptake rate greater than the liquid uptake rate exhibited by an otherwise identical absorbent structure without any wettable staple fiber. Also disclosed is an absorbent garment containing such an absorbent structure.

39 Claims, 4 Drawing Sheets

ABSORBENT STRUCTURE COMPRISING SUPERABSORBENT, STAPLE FIBER, AND BINDER FIBER

This application is a continuation-in-part of U.S. patent application Ser. No. 08/157,802 filed Nov. 23, 1993, abandoned.

BACKGROUND OF THE INVENTION

1. Field of the Invention

The present invention relates to an absorbent structure suitable for use in absorbent products. More particularly, the present invention relates to an absorbent structure comprising superabsorbent material, wettable staple fiber, and wettable binder fiber.

2. Description of the Related Art

The purpose of disposable absorbent products is typically body waste management. In order to manage liquid body waste, the absorbent structure within an absorbent product must generally be able to first uptake the liquid into the absorbent product, then distribute the liquid within the absorbent product, and then retain the liquid within the absorbent product.

It is generally important that the absorbent structure uptake the liquid at about the rate of delivery of the liquid to the absorbent product or else the liquid may run off the absorbent structure's surface and not be present for the absorbent structure to distribute and retain within the absorbent product. That is, if the liquid uptake rate of the absorbent structure is less than the delivery rate of the liquid to the absorbent product, there exists the possibility of leakage of the liquid from the absorbent product.

In addition, if the distribution of the liquid by the absorbent structure within the absorbent product is not adequate, the efficiency of the absorbent structure's utilization will be low. Typically, commercially available absorbent products are designed with an excess absolute liquid saturated retention capacity. Thus, the absorbent structure in the absorbent product is often not fully utilized. An increase in distribution efficiency of the liquid by the absorbent material would potentially allow either a higher realized liquid saturation level for an absorbent product using the same amount of absorbent structure or the use of less absorbent structure to achieve the same realized liquid saturation level in the absorbent product without any increase in liquid leakage. The use of less absorbent structure to achieve the same realized liquid saturation level in an absorbent product will typically result in less absorbent product being disposed of to the environment.

Absorbent structures suitable for use in absorbent products are generally well known. Originally, it was a general practice to form absorbent structures comprising an absorbent fibrous matrix entirely from wood pulp fluff, such as a batt of comminuted wood pulp fluff. Given the relatively low amount of liquid absorbed by wood pulp fluff on a gram of liquid absorbed per gram of wood pulp fluff basis, it is necessary to employ relatively large quantities of wood pulp fluff, thus, necessitating the use of relatively large, thick absorbent structures.

In order to enhance the absorbent capacity of such absorbent structures, it is common to incorporate into them a superabsorbent material. Such superabsorbent materials are generally capable of absorbing at least about 10 times their weight in water. The introduction of superabsorbent materials into such absorbent structures allows for the use of less wood pulp fluff, since the superabsorbent material generally has a higher liquid absorption capacity on a gram per gram basis than the wood pulp fluff. Moreover, such superabsorbent materials are less pressure sensitive than wood pulp fluff. Thus, the use of the superabsorbent materials generally allows for the production and use of a smaller, thinner absorbent product.

Absorbent structures generally comprise a relatively low amount (less than about 50 weight percent) of the superabsorbent material. There are several reasons for this. For example, superabsorbent materials employed in known absorbent products have generally not had a liquid uptake rate which would allow them to absorb liquid at the rate at which the liquid is applied to the absorbent products during use. Accordingly, the fibrous matrix of the absorbent structure must often serve as a reservoir which will hold the liquid discharged thereon until the liquid is absorbed by the superabsorbent material. Superabsorbent materials with faster liquid uptake rates can absorb liquid faster, but such superabsorbent materials often exhibit gel blocking. Gel blocking refers to the situation wherein the particles of superabsorbent material deform during swelling and block the interstitial spaces between the particles, or between the particles and the fibrous matrix, thus preventing the flow of liquid through the interstitial spaces. At lower levels of addition of the superabsorbent material, the fibrous matrix serves to keep the particles of superabsorbent material separated from one another and provides a capillary structure which allows a liquid to pass through the fibrous matrix to reach the superabsorbent materials located remote from the point at which the liquid is applied to the absorbent product.

Dispersing such superabsorbent materials in a fibrous matrix at relatively low concentrations, in order to avoid gel blocking, results in the need to locate superabsorbent materials in areas relatively remote from the point at which the liquid is applied to the absorbent product. That is, in order to introduce useful amounts of superabsorbent material into an absorbent structure, and yet disperse such superabsorbent materials sufficiently to prevent gel blocking, it is necessary for the absorbent structures to have relatively large surface areas and to be relatively thick. For the above reasons, it is still typically necessary to use relatively low concentrations of superabsorbent material and enough fibrous matrix to permit the superabsorbent materials to function in the desired manner.

SUMMARY OF THE INVENTION

It is desirable to produce an absorbent structure able to meet or exceed the performance characteristics of known absorbent structures while containing a relatively high concentration of superabsorbent material. It is also desired to produce an absorbent structure which is able to rapidly absorb a discharged liquid under pressures typically encountered during use and to retain the absorbed liquid under pressures typically encountered during use. Further, it is desired to produce an absorbent structure which has a lower volume and mass than known absorbent structures while having generally the same realized liquid saturation level as the known absorbent structures, thus, allowing for easier, more efficient disposal.

These and other related goals are achieved by an absorbent structure comprising a superabsorbent material, a wettable staple fiber, and a wettable binder fiber, wherein the absorbent structure exhibits improved liquid uptake rates as compared to an otherwise identical absorbent structure which does not comprise a wettable staple fiber.

In one embodiment of the present invention, an absorbent structure comprises from about 25 to about 99 weight percent superabsorbent material, wherein the superabsorbent material is capable of absorbing an amount of water at least about 10 times the weight of the superabsorbent material, from greater than 0 to about 35 weight percent wettable staple fiber; and from greater than 0 to about 40 weight percent wettable binder fiber, wherein all weight percents are based on the total weight of the superabsorbent material, wettable staple fiber, and wettable binder fiber in the absorbent structure; and wherein the absorbent structure exhibits a liquid uptake rate at least about 2 times greater than the liquid uptake rate exhibited by an otherwise identical absorbent composition without any wettable staple fiber for any of three 60 milliliter insults of synthetic urine at 23° C. applied at a rate of 15 milliliters/second with 5 minutes between each insult, wherein the insults are applied to the absorbent structure with an absolute liquid saturated retention capacity of at least about 240 milliliters.

In another aspect, it is desirable to provide a thin, absorbent garment, such as an infant diaper, which garment employs an absorbent structure having a relatively small volume and a high concentration of superabsorbent material. Further, it is desirable to provide an absorbent garment which has a relatively small volume and a relatively high capacity.

In one embodiment, these goals are achieved in an absorbent garment comprising a bodyside liner, an outer cover, and an absorbent structure positioned between the bodyside liner and the outer cover; wherein the absorbent structure comprises a superabsorbent material, a wettable staple fiber, and a wettable binder fiber.

DETAILED DESCRIPTION OF THE PREFERRED EMBODIMENT

Figure 1:
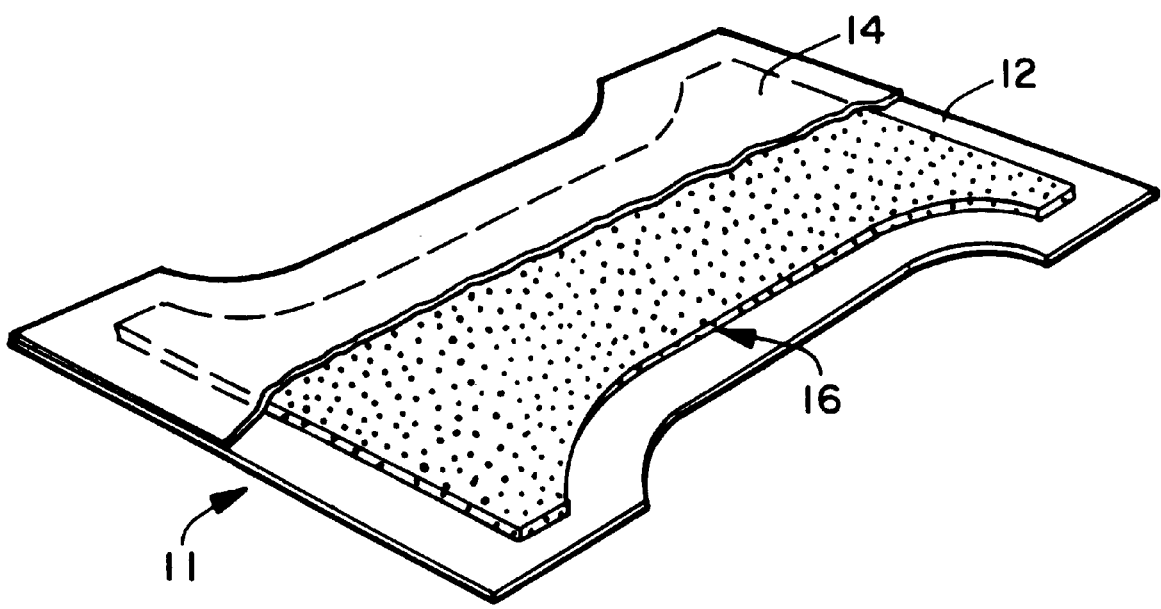
FIG. 1 is a perspective view of one embodiment of a disposable absorbent garment according to the present invention.

In one aspect, the present invention concerns an absorbent structure and an absorbent garment possessing improved, desirable liquid-handling characteristics achievable by the careful selection and use of superabsorbent material, wettable staple fiber, and wettable binder fiber employed in forming such absorbent structures and absorbent garments.

As used herein, the term "superabsorbent material" refers to a high-absorbency material. Such high-absorbency materials are generally capable of absorbing an amount of a liquid, such as water, synthetic urine, a 0.9 weight percent aqueous saline solution, or other bodily liquids such as menses or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The superabsorbent material may be formed from an organic hydrogel material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines. Other suitable hydrogel polymers include hydrolyzed acrylonitrile-grafted starch, acrylic acid-grafted starch, and isobutylene maleic anhydride copolymers and mixtures thereof. The hydrogel polymers are preferably lightly crosslinked to render the material substantially water insoluble yet water swellable. Crosslinking may, for example, be by irradiation or covalent, ionic, van der Waals, or hydrogen bonding. Suitable superabsorbent materials are typically available from various commercial vendors, such as The Dow Chemical Company, Hoechst Celanese, Allied Colloids Limited, or Stockhausen, Inc.

The superabsorbent material employed in the absorbent structures of the present invention suitably should be able to absorb a liquid under an applied load. For the purposes of this application, the ability of a superabsorbent material to absorb a liquid under an applied load and thereby perform work is quantified as the Absorbency Under Load (AUL) value. The AUL value is expressed as the amount (in grams) of an aqueous 0.9 weight percent sodium chloride solution which the superabsorbent material can absorb per gram of superabsorbent material under a load of about 0.3 pounds per square inch (approximately 2.0 kilopascals) while restrained from swelling in the plane normal to the applied load. The superabsorbent material employed in the absorbent structures of the present invention suitably exhibit an AUL value of at least about 15, more suitably of at least about 20, and up to about 50. The method by which the AUL value is determined is set forth in detail below in connection with the examples which follow.

In one embodiment of the present invention, the superabsorbent material is in the form of particles which, in the unswollen state, have maximum cross-sectional diameters within the range of from about 50 microns to about 1000 microns, preferably within the range of from about 100 microns to about 800 microns, as determined by sieve analysis according to American Society for Testing and Materials (ASTM) test method D-1921. It is understood that the particles of superabsorbent material falling within the ranges described above may comprise solid particles, porous particles, or may be agglomerated particles comprising many smaller particles agglomerated into particles falling within the described size ranges.

The superabsorbent material is present in the absorbent structure of the present invention in an amount of from about 25 to about 99 weight percent, beneficially from about 30 to about 99 weight percent, more beneficially from about 50 to about 99 weight percent, suitably from about 65 to about 95 weight percent, and more suitably from about 75 to about 90 weight percent, based on total weight of the superabsorbent material, wettable staple fiber, and wettable binder fiber in the absorbent structure.

Because the superabsorbent materials present in the absorbent structures of the present invention can be present in high concentrations, the absorbent structures of the present invention can be relatively thin and light weight, have a relatively small volume, and still function in a desirable manner.

As used herein, the term "staple fiber" is meant to refer to a natural fiber or a length cut from, for example, a manufactured filament. Such staple fibers are intended to act in the absorbent structure of the present invention as a temporary reservoir for liquid and also as a conduit for liquid distribution.

Preferably, the staple fibers used in the absorbent structures herein should range in length from about 0.1 to about 15 cm, and suitably from about 0.2 to about 7 cm. Staple fibers of these size characteristics, when combined with the wettable binder fiber and superabsorbent material herein, help to impart desirable bulk, improved liquid acquisition, liquid distribution and strength characteristics, and/or desirable flexibility and resilience properties to the absorbent structures of this invention.

As used herein, the term "wettable" is meant to refer to a fiber which exhibits a liquid, such as water, synthetic urine, or a 0.9 weight percent aqueous saline solution, in air contact angle of less than 90°. As used herein, the contact angle may be determined, for example, as set forth by Robert J. Good and Robert J. Stromberg, Ed., in "Surface and Colloid Science—Experimental Methods", Vol. 11, (Plenum Press, 1979). Suitably, a wettable fiber refers to a fiber which exhibits a synthetic urine in air contact angle of less than 90° at a temperature between about 0° C. and about 100° C. and suitably at ambient conditions, such as about 23° C.

Suitable wettable fibers may be formed from intrinsically wettable fibers or may be formed from intrinsically hydrophobic fibers having a surface treatment thereon which renders the fiber hydrophilic. When surface treated fibers are employed, the surface treatment is desirably nonfugitive. That is, the surface treatment desirably does not wash off the surface of the fiber with the first liquid insult or contact. For the purposes of this application, a surface treatment on a generally hydrophobic polymer will be considered to be nonfugitive when a majority of the fibers demonstrate a liquid in air contact angle of less than 90° for three consecutive contact angle measurements, with drying between each measurement. That is, the same fiber is subjected to three separate contact angle determinations and, if all three of the contact angle determinations indicate a contact angle of liquid in air of less than 90°, the surface treatment on the fiber will be considered to be nonfugitive. If the surface treatment is fugitive, the surface treatment will tend to wash off of the fiber during the first contact angle measurement, thus, exposing the hydrophobic surface of the underlying fiber and will demonstrate subsequent contact angle measurements greater than 90°.

A wide variety of staple fiber materials can be employed in the absorbent structures herein. Staple fibers useful in the present invention may be formed from natural or synthetic materials and may include cellulosic fibers such as wood pulp fibers and modified cellulose fibers, textile fibers such as cotton or rayon, and substantially nonabsorbent synthetic polymeric fibers.

For reasons of availability and cost, cellulosic fibers will frequently be preferred for use as the staple fiber component of the absorbent structures of this invention. Most preferred are wood pulp fibers. However, other cellulosic fiber materials may also be used as the staple fiber.

Another preferred type of staple fiber useful herein comprises substantially nonabsorbent, crimped synthetic polymeric fibers. The individual fibers of this type are in and of themselves substantially nonabsorbent. Thus, such fibers should be prepared from a synthetic polymer material which does not substantially swell or gel in the presence of liquids, such as urine or menses, typically encountered in disposable absorbent products. Suitable polymeric materials which may be used to prepare the desired staple fibers include polyesters, polyolefins, polyacrylics, polyamides, and polystyrenes. Suitably, staple fibers are made of polyethylene, polypropylene, or polyethylene terephthalate.

The staple fibers used herein may also be crimped in order for the resulting absorbent structure to have the desired resilience and resistance to bunching during use in absorbent products. Crimped staple fibers are those which have a continuous wavy, curvy or jagged character along their length. Fiber crimping of this sort is described more fully in U.S. Pat. No. 4,118,531, incorporated herein by reference.

The wettable staple fibers should be present in the absorbent structure of the present invention in an amount effective to result in the desired increase in liquid uptake rate as compared to an otherwise identical absorbent structure that does not comprise any wettable staple fiber. Typically, the wettable staple fibers should be present in the absorbent structure of the present invention in an amount from greater than 0 to about 35 weight percent, suitably from about 1 to about 30 weight percent, and more suitably from about 5 to about 20 weight percent wettable staple fiber, with all weight percents based on the total weight of the wettable staple fiber, superabsorbent material, and wettable binder fiber in the absorbent structure.

As used herein, the term "otherwise substantially identical absorbent structure without any wettable staple fiber," and other similar terms, are intended to refer to a control absorbent structure that is prepared using substantially identical materials and a substantially identical process as compared to an absorbent structure of the present invention, except that the control absorbent structure does not comprise or is not prepared with the wettable staple fiber described herein but, instead, comprises an amount of additional binder fiber substantially identical to the amount of wettable staple fiber used in the absorbent structure of the present invention. As such, the otherwise substantially identical absorbent structure without any wettable staple fiber and the absorbent structure of the present invention will generally have substantially identical basis weights. As a result of not comprising the wettable binder fiber, the otherwise substantially identical absorbent structure generally will not exhibit the desired absorbent properties described herein as compared to an absorbent structure of the present invention.

As used herein, the term "binder fiber" is meant to refer to a fiber that acts to form a composite web when the binder fiber is in its final form in the absorbent structure herein. As such, the binder fibers interact with each other in some manner to form a composite web. Such interaction of the binder fibers may be in the form of entanglement or an adhesive interaction whereby the binder fibers are treated as, for example, by heating the binder fibers above their softening point temperature and allowing the binder fibers to contact each other to form adhesive bonds. Once treated in such a manner, the binder fibers cannot be reclaimed in their original form. This is in contrast to the staple fibers and superabsorbent material which substantially retain their individual form, although such staple fibers and superabsorbent material may be adhered to by the binder fibers in the absorbent structures of the present invention.

The binder fiber may generally be formed from any thermoplastic composition capable of extrusion into fibers. Examples of such thermoplastic compositions include polypropylene and polyethylene, polyesters such as polyethylene terephthalate, polyamides such as nylon, as well as copolymers and blends of these and other thermoplastic polymers.

A suitable binder fiber for the present invention comprises meltblown fibers formed from a hydrophilic nylon copolymer material. Such meltblown fibers are typically very fine fibers prepared by extruding liquified, or melted, fiber-forming copolymer through orifices in a die into a high velocity gaseous stream. The fibers are attenuated by the gaseous stream and are subsequently solidified. The resulting stream of solidified binder fibers can be collected as, for example, on a screen disposed in the gaseous stream, as an entangled coherent fibrous mass. Such an entangled fibrous mass is characterized by extreme entanglement of the binder fibers. This entanglement provides coherency and strength to the resulting web structure. Such entanglement also adapts the web structure to constrain or entrap the staple fiber and the superabsorbent material within the structure after the staple fiber and the superabsorbent material have been incorporated into the web structure, either during or after formation of the web structure. The binder fibers are entangled sufficiently that it is generally impossible to remove one complete binder fiber from the mass of binder fibers or to trace one binder fiber from beginning to end.

As used herein, the constraining or entrapment of the staple fiber and the superabsorbent material within the web structure is meant to represent that the staple fiber and the superabsorbent material are substantially immobilized, such that the staple fiber and the superabsorbent material are not free to substantially move or migrate within or out of the web structure. Such constraining or entrapment may be, for example, by adhesive means or by the entanglement of the binder fibers of the web structure.

The binder fiber used herein may be circular but may also have other cross-sectional geometries such as elliptical, rectangular, triangular, or multi-lobal.

A suitable binder fiber of the present invention may comprise a conventional nylon polymer chain. Nylon polymers are polyamides which can be obtained, for example, by the condensation polymerization reaction of a polyacid and a polyamine. Depending upon the nature of the reactants employed, various forms of nylon can be utilized as the nylon component of the copolymers herein. Examples of these various forms of nylon include nylon-6,6; nylon-6,10; and nylon-6. Methods for preparing these nylon-type polyamides are well known and described in the art. Particularly suitable is nylon-6 which can be prepared by the polymerization of caprolactam.

In addition to the nylon component, the hydrophilic nylon polymer will also generally comprise a hydrophilizing polymeric component. Any polymeric component capable of being polymerized with the nylon component, and capable of hydrophilizing the resultant copolymeric material to render it wettable according to the definition of the present invention, is suitable for use in the present invention. One hydrophilizing polymeric component suitable for use in the present invention comprises polyethylene oxide. In one specific embodiment of the present invention, the hydrophilic nylon copolymer comprises a nylon component formed from poly(pentamethylene carbonamide) (nylon 6) and polyethylene oxide formed from polyethylene oxide diamine. Such nylon-6/polyethylene copolymers will suitably have a number average molecular weight within the range of from about 5,000 to about 100,000, more suitably from about 20,000 to about 30,000.

Polyethylene oxide diamine materials are commercially available from the Jefferson Chemical Company under the trade designation JEFFAMINE™. Exemplary of other suitable hydrophilic nylon polymeric materials include a graft copolymer of nylon, such as nylon-6, and a low molecular weight poly(dimethylacrylamide), and block copolymers of nylon and a random poly(dioxaamide).

The fiber-forming hydrophilic nylon copolymer may be either a block or a graft copolymer formed from its respective nylon and hydrophilizing polymeric components. Processes for preparing both block and graft copolymers, in general, are known in the art. Whether the copolymer useful for the fibers herein is block or graft will depend upon the particular nature of the hydrophilizing polymeric component which is utilized in forming the copolymer.

The wettable binder fibers should be present in the absorbent structure of the present invention in an amount effective to provide sufficient support or bulk to the absorbent structure and to effectively constrain or entrap the wettable staple fiber and superabsorbent material. Typically, the wettable binder fibers should be present in the absorbent structure of the present invention in an amount from greater than 0 to about 40 weight percent, suitably from about 1 to about 30 weight percent, more suitably from about 5 to about 20 weight percent wettable binder fiber, with all weight percents based on the total weight of the wettable staple fiber, superabsorbent material, and wettable binder fiber in the absorbent structure.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The absorbent structure of the present invention preferably comprises a fibrous matrix comprising the wettable binder fiber wherein the fibrous matrix constrains or entraps the wettable staple fiber and the superabsorbent material.

The fibrous matrix may be formed by air-laying fibers, through a spunbond or meltblown process, a carding process, a wet-laid process, or through essentially any other means, known to those skilled in the art, for forming a fibrous matrix.

Methods of incorporating the superabsorbent material and wettable staple fiber into the fibrous matrix are known to those skilled in the art. Suitable methods include incorporating the superabsorbent material and wettable staple fiber into the matrix during formation of the matrix, such as by air laying the fibers of the fibrous matrix and the superabsorbent material and/or wettable staple fiber at the same time or wet-laying the fibers of the fibrous matrix and the superabsorbent material and/or wettable staple fiber at the same time. Alternatively, it is possible to apply the superabsorbent material and/or wettable staple fiber to the fibrous matrix after formation of the fibrous matrix. Other methods include sandwiching the superabsorbent material between two sheets of material, at least one of which is fibrous and liquid permeable. The superabsorbent material may be generally uniformly located between the two sheets of material or may be located in discrete pockets formed by the two sheets. It is preferable that the wettable staple fiber be generally uniformly distributed within the fibrous matrix. However, the wettable staple fiber may be nonuniformly distributed as long as the desired liquid uptake rates of the absorbent structure are still achieved.

The fibrous matrix may be in the form of a single, integrally formed layer or of a composite comprising multiple layers. If the fibrous matrix comprises multiple layers, the layers are preferably in liquid communication with one another, such that, a liquid present in one fibrous layer can flow or be transported to the other fibrous layer. For example, the fibrous layers may be separated by cellulosic tissue wrap sheets known to those skilled in the art.

The superabsorbent material may be distributed in the individual layers in a generally uniform manner or may be present in the fibrous layers as a layer or other nonuniform distribution.

When the fibrous matrix comprises a single, integrally formed layer, the concentration of superabsorbent material may increase along the thickness of the fibrous matrix in a gradual, nonstepwise fashion or in a more stepwise fashion. Similarly, the density may decrease through the thickness in a nonstepwise manner or in a stepwise manner.

The absorbent structures of the present invention may generally be of any size or dimension as long as the absorbent structure exhibits the desired absorbent characteristics as described herein. Typically, the absorbent structures will have a volume of at least about 18 cubic centimeters, such as with a width of about 6 centimeters, a length of about 6 centimeters, and a depth of about 0.5 centimeter. Suitably, the absorbent structure will have a volume of at least about 60 cubic centimeters, such as with a width of about 10 centimeters, a length of about 6 centimeters, and a depth of about 1 centimeter.

The absorbent structure of the present invention may also be used or combined with other absorbent structures, with the absorbent structure of the present invention being used as a separate layer or as an individual zone or area within a larger, composite absorbent structure. The absorbent structure of the present invention may be combined with other absorbent structures by methods well known to those skilled in the art, such as by using adhesives or simply by layering the different structures together and holding together the composite structures with, for example, tissue.

The absorbent structures according to the present invention are suited to absorb many liquids, such as water, saline, and synthetic urine, and body liquids such as urine, menses, and blood, and are suited for use in absorbent garments such as diapers, adult incontinent products, and bed pads; in catamenial devices such as sanitary napkins, and tampons; and in other absorbent products such as wipes, bibs, wound dressings, and surgical capes or drapes. Accordingly, in another aspect, the present invention relates to an absorbent garment comprising an absorbent structure as described herein.

Use of the described absorbent structures in absorbent garments allows for the formation of an absorbent garment which is able to rapidly receive a discharged liquid and, yet, which garment is thin.

Such absorbent garments generally comprise a liquid-permeable bodyside liner, a liquid-impervious outer cover, and an absorbent structure, such as the absorbent structures of the present invention, located between the bodyside liner and outer cover.

Exemplary absorbent garments are generally described in U.S. Pat. Nos. 4,710,187; 4,762,521; 4,770,656; 4,798,603; and U.S. Ser. No. 07/757,760, filed Sep. 11, 1991 in the name of Hansen et al., which references are incorporated herein by reference.

In one embodiment of the present invention, an absorbent garment is provided, which absorbent garment comprises a bodyside liner, an outer cover, and an absorbent structure comprising a superabsorbent material, a wettable staple fiber, and a wettable binder fiber, wherein the absorbent structure is positioned between the bodyside liner and the outer cover.

Those skilled in the art will recognize materials suitable for use as the bodyside liner and outer cover. Exemplary of materials suitable for use as the bodyside liner are liquid-permeable materials, such as spunbonded polypropylene or polyethylene having a basis weight of from about 15 to about 25 grams per square meter. Exemplary of materials suitable for use as the outer cover are liquid-impervious materials such as polyolefin films, as well as liquid-pervious or water-vapor-pervious materials such as microporous polyolefin films.

While the preferred embodiment of the invention will be described in terms of the use of the absorbent structure in an infant diaper, it is to be understood that the absorbent structure is equally suited for use in other absorbent garments known to those skilled in the art.

Turning now to the drawings, FIG. 1 illustrates a disposable diaper 11 according to one embodiment of the present invention. Disposable diaper 11 includes an outer cover 12, a bodyside liner 14, and an absorbent structure 16, located between the outer cover 12, and the bodyside liner 14. Absorbent structure 16 is an absorbent structure according to the present invention. Specifically, in the illustrated embodiment, absorbent structure 16 comprises a web of wettable binder fibers which functions as the containment means and constrains superabsorbent material and wettable staple fiber. Because absorbent structure 16 is formed in accordance with the present invention, the absorbent structure 16 has a liquid uptake rate value which renders it suitable for use in the disposable diaper 11.

Absorbent garments and structures according to all aspects of the present invention are generally subjected, during use, to multiple insults of a body liquid. Accordingly, the absorbent garments and structures are desirably capable of absorbing multiple insults of body liquids in quantities to which the absorbent garments and structures will be exposed during use. The insults are generally separated from one another by a period of time.

The absorbent structures of the present invention have been found to exhibit improved liquid uptake rates as compared to an otherwise identical absorbent structure not comprising a wettable staple fiber. In particular, the absorbent structures of the present invention have been found to exhibit liquid uptake rates that are at least about 2, beneficially at least about 2.5, more beneficially at least about 5, and suitably at least about 10, and up to about 25 times the liquid uptake rate for any of three, suitably for the third of three, more suitably for each of three, about 60 milliliter insults of a liquid such as a 0.9 weight percent aqueous saline solution, or synthetic urine, at about 23° C. applied at a rate of about 15 milliliters/second with about 5 minutes between each insult, exhibited by an otherwise identical absorbent structure that does not comprise a wettable staple fiber wherein the absorbent structure to which the liquid insults are applied has an absolute liquid saturated retention capacity of at least about 240 milliliters.

As used herein, the "absolute liquid saturated retention capacity" of an absorbent structure is meant to represent the maximum amount of liquid the absorbent structure can retain when given a sufficient amount of time to reach 100 percent saturation and when an externally applied pressure of about 0.5 psi is applied to the saturated structure. As used herein, the application of three 60 milliliter insults of liquid to an absorbent structure with an absolute liquid saturated retention capacity of at least about 240 milliliters is meant to represent no more than about 75 percent of the absolute liquid saturated retention capacity of the absorbent structure being tested, such that each 60 milliliter insult represents no more than about 25 percent of the absolute liquid saturated retention capacity of the absorbent structure being tested. Such a relationship between the liquid insults and the absolute liquid saturated retention capacity of the absorbent structure being tested is meant to ensure that the absorbent structure has a sufficient absolute liquid saturated retention capacity so as to be able to effectively absorb the three liquid insults with a minimum of liquid leakage and so as to result in meaningful results when evaluating the absorbent structure for liquid uptake rate.

The absorbent structures of the present invention suitably have a specific liquid saturated retention capacity on a gram of liquid absorbed to a gram of absorbent structure basis of about 8 g/g to about 40 g/g, beneficially of about 10 g/g to about 35 g/g, and more beneficially of about 15 g/g to about 30 g/g.

The absorbent structures of the present invention suitably have a basis weight of about 100 grams per square meter (g/sm) to about 1000 g/sm, beneficially of about 200 g/sm to about 800 g/sm, and more beneficially of about 300 g/sm to about 700 g/sm.

The absorbent structures of the present invention suitably have a density of about 0.03 gram per cubic centimeter (g/cc) to about 0.5 g/cc, beneficially of about 0.05 g/cc to about 0.45 g/cc, and more beneficially of about 0.08 g/cc to about 0.4 g/cc.

The absorbent structures of the present invention preferably also exhibit an improved distribution of liquid as compared to an otherwise identical absorbent structure that does not comprise a wettable staple fiber.

Test Methods

Synthetic Urine

The synthetic urine composition referenced herein comprises 0.31 gram monobasic calcium phosphate monohydrate ($CaH_4(PO_4)_2H_2O$), 0.68 gram monobasic potassium phosphate ($KH_2PO_4$), 0.48 gram magnesium sulphate heptahydrate ($MgSO_4.7H_2O$), 1.33 grams potassium sulphate ($K_2SO_4$), 1.24 grams tribasic sodium phosphate dodecahydrate ($Na_3PO_4.12H_2O$), 4.4 grams sodium chloride (NaCl), 3.16 grams potassium chloride (KCl), 8.56 grams of urea ($CO(NH_2)_2$), 0.1 gram Pluronic 10R8 surfactant (a nonionic surfactant commercially available from BASF-Wyandotte Corporation) and 1 gram methyl paraben and 1 gram Germall 115 preservative (commercially available from Santell Chemical Company, Chicago, Ill.) per liter, using distilled water as the solvent. The components are added to 900 milliliters of distilled water in the order given and each dissolved before the next component is added. The solution is finally diluted to one liter.

Absorbency Under Load (AUL)

The Absorbency Under Load (AUL) is a test which measures the ability of an absorbent material to absorb a liquid (0.9 weight percent solution of sodium chloride in distilled water) while under an applied load or restraining force.

Figure 2:
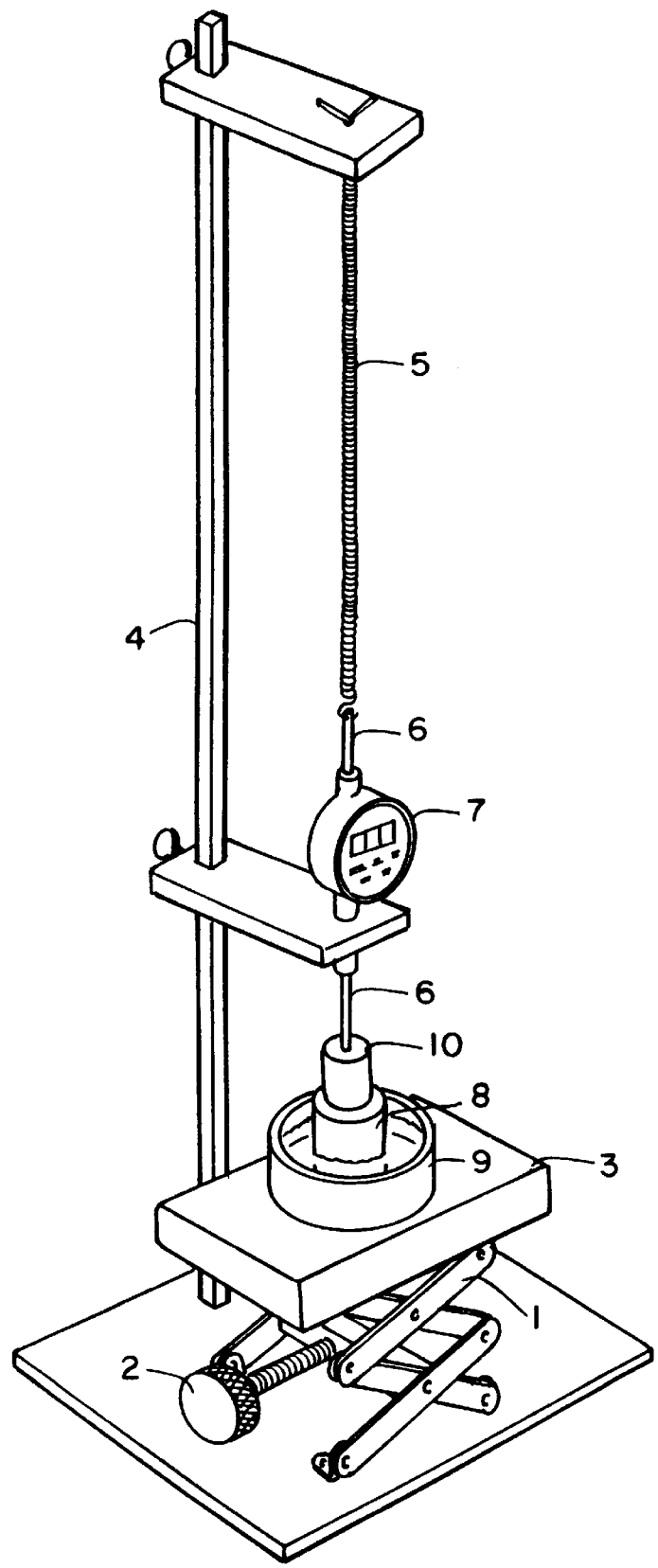
FIG. 2 is an illustration of the equipment employed in determining the Absorbency Under Load (AUL) value of superabsorbent material.

Referring to FIG. 2, the apparatus and method for determining AUL values will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9, which contains the saline solution to be absorbed. A weight 10 rests on top of a spacer disc (not visible) resting on top of the superabsorbent material sample (not visible).

The sample cup 8 consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41) which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of about 0.3 pound per square inch. The sample cup is placed in the Petri dish on the platform of the laboratory jack raised up until it contacts the tip of the probe. The meter is zeroed. A sufficient amount of saline solution is added to the Petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value expressed as grams saline solution absorbed per gram of absorbent. If desired, the readings of the modified thickness meter can be continuously inputted to a computer (Mitutoyo Digimatic Miniprocessor DP-2 DX) to make the calculations and provide AUL readings. As a cross-check, the AUL value can also be determined by determining the weight difference between the sample cup before and after the test, the weight difference being the amount of solution absorbed by the sample.

Liquid Uptake Rate

As used herein, the "liquid uptake rate" is defined (in milliliters/second (mls/sec)) as the volume of liquid (in milliliters) used to insult an absorbent garment, absorbent structure or containment means containing superabsorbent material divided by the length of time (in seconds) required for the absorbent garment, absorbent structure or containment means to absorb the liquid insult. The volume of each of three equal liquid insults is set at about 25 percent of the absolute saturated liquid retention capacity of the material being tested. For example, each of three equal 60 milliliter insults (180 milliliters total) are used when the object to be tested has an absolute liquid saturated retention capacity of at least about 240 milliliters, of room temperature (~23° C.) synthetic urine. The liquid insults are applied to material in a localized area (about 1 square centimeter) at a rate of 15 milliliters per second, with a period, for example, of about 5 minutes between each insult. The absorption time commences when the liquid insult initially contacts the surface of the object being tested and ends when the liquid can no longer be seen on the surface of the tested object.

Figure 3:
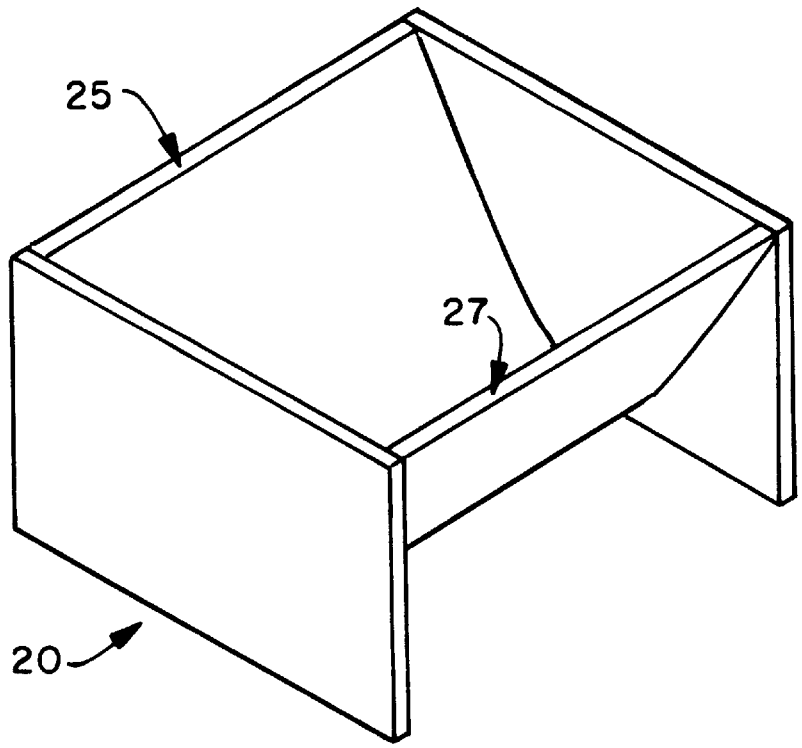
FIG. 3 is a perspective illustration of the cradle-shaped specimen holder employed in determining the liquid uptake rate of an absorbent structure.
Figure 4:
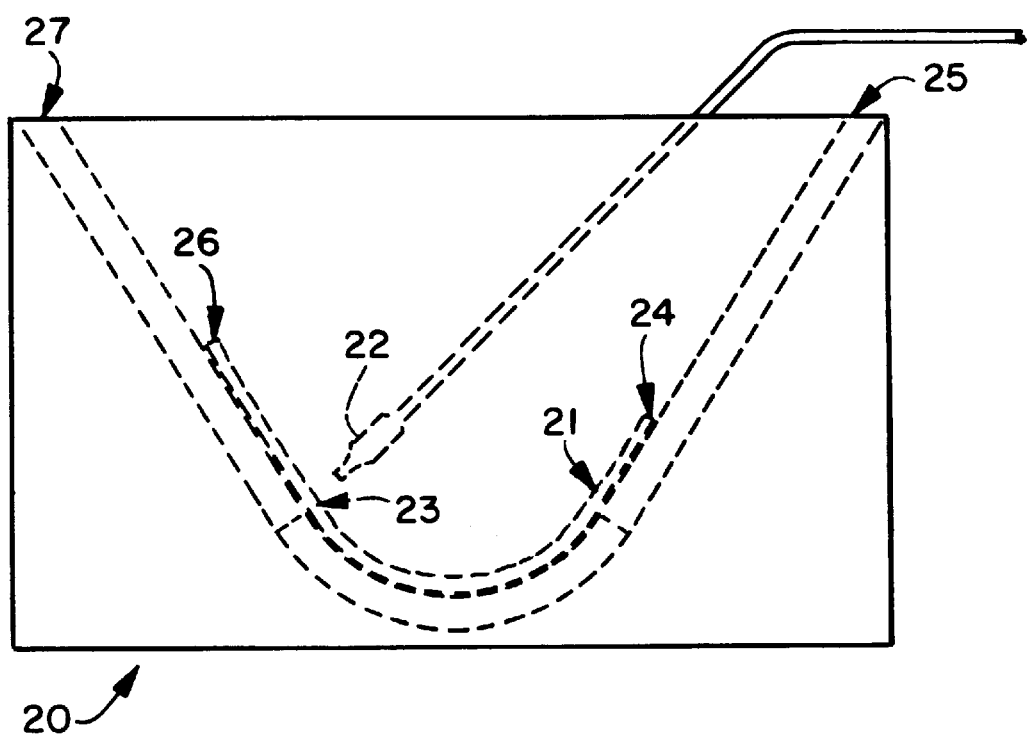
FIG. 4 is a side illustration of the equipment employed in determining the liquid uptake rate of an absorbent structure.

Referring to FIGS. 3 and 4, the liquid uptake rate value is determined as follows. The object 21 to be tested suitably having a length of about 9 inches (about 23 cm) and a width of about 3 inches (about 8 cm), a moisture content of less than about 7 weight percent, and an absolute liquid saturated retention capacity of at least about 240 ml, is placed in a cradle-shaped specimen holder 20. The test object 21 is placed in the cradle-shaped specimen holder 20 with the back end 24 of the test object 21 about 6.5 inches (about 17 cm) from the back 25 of the cradle-shaped specimen holder 20, and the front end 26 of the test object 21, about 4.5 inchs (about 11 cm) from the front 27 of the cradle-shaped specimen holder 20. A target zone 23 is marked about 3.25 inches (about 8 cm) from the front end 26 of test object 21.

A nozzle 22 having about a 3 millimeter diameter orifice is placed a distance of about ¼ inch (about 0.6 cm) away from the target zone 23 at an angle of about 60° from a generally horizontal major face of the test object 21. The nozzle 22 may be attached, for example, to a pump equipped with a pulse suppressor (not shown) for ease of delivery of the liquid to the nozzle 22.

A first insult of synthetic urine is applied to the test object 21 from the nozzle 22 at an average rate of about 15 milliliters per second until about 60 milliliters has been applied. After 5 minutes another 60 milliliters is applied. After another 5 minutes a third 60 milliliter insult is applied.

The time for each 60 milliliter insult to be absorbed by the test object 21 is recorded. Each 60 milliliter insult is divided by the time period for its absorption and is reported as the liquid uptake rate value (in mls/sec) for that insult.

Liquid Saturated Retention Capacity

Figure 5:
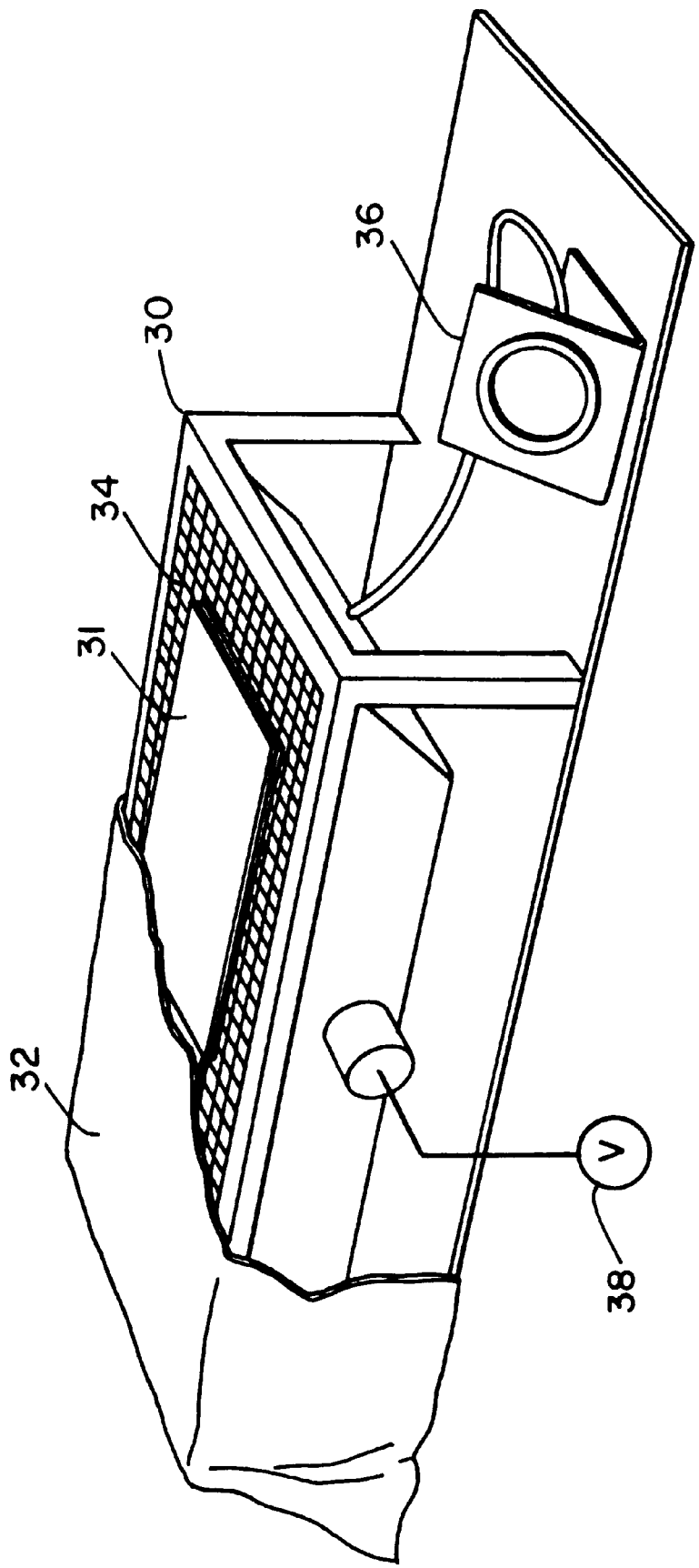
FIG. 5 is an illustration of the equipment employed in determining the liquid saturated retention capacity of an absorbent structure.

The liquid saturated retention capacity is determined as follows. The material to be tested, having a moisture content of less than about 7 weight percent, is weighed and submerged in an excess quantity of room temperature (about 23° C.) synthetic urine. The material to be tested is allowed to remain submerged for about 20 minutes. After the 20 minute submerging, the material 31 is removed and, referring to FIG. 5, placed on a TEFLON™ coated fiberglass screen 34 having 0.25 inch (0.6 cm) openings (commercially available from Taconic Plastics Inc., Petersburg, N.Y.) which, in turn, is placed on a vacuum box 30 and covered with a flexible rubber dam material 32. A vacuum of about 0.5 pound per square inch (about 3.5 kilopascals) is drawn on the vacuum box for a period of about 5 minutes with the use of, for example, a vacuum gauge 36 and a vacuum pump (38). The material being tested is then removed from the screen and weighed. The amount of liquid retained by the material being tested is determined by subtracting the dry weight of the material from the wet weight of the material (after application of the vacuum), converting the net weight to milliliters by using the density of the test liquid, and is reported as the liquid saturated retention capacity in milliliters of liquid retained. For relative comparisons, this value can be divided by the weight of the material 31 to give the specific liquid saturated retention capacity in grams of liquid retained per gram of tested material. If material, such as superabsorbent material or fiber, is drawn through the fiberglass screen while on the vacuum box, a screen having smaller openings should be used. Alternatively, a piece of tea bag or similar material can be placed between the material and the screen and the final value adjusted for the liquid retained by the tea bag or similar material.

EXAMPLES

Example 1

Absorbent structures are prepared comprising a superabsorbent material, a wettable staple fiber and a wettable binder fiber. For the superabsorbent material, a poly(acrylic acid) high-absorbency material, commercially available from Hoechst Celanese under the trade name designation IN 5000P, is used in Samples 1 through 3; and a poly(acrylic acid) high-absorbency material, commercially available from The Dow Chemical Company under the trade name designation DRYTECH™ 534, is used in Samples 4 through 8. In Sample 2, the wettable staple fiber is a rayon of 3 denier, has a round cross section, and is cut to 1.5 inches lengths. In Samples 3 and 5, the wettable staple fiber is a rayon of 2.4 denier, has a trilobal cross section, and is cut to 1.5 inches lengths. In Samples 7 and 8, the wettable staple fiber is a wood pulp fluff. For the wettable binder fiber, a hydrophilic nylon-6, polyethylene oxide diamine blockcopolymer, which is commercially available from Allied-Signal, Inc. under the trade name designation HYDROFIL™, is used for each sample.

The wettable binder fiber is meltblown into an entangled composite web with the superabsorbent material fed into the meltblown stream and the staple fiber fed into the composite web structure with a picker roll. The absolute and relative basis weight amounts used of the different materials for various samples is indicated in Table 1. The basis weight amounts are given in grams per square meter (g/sm) of absorbent composition formed. The samples are evaluated for liquid saturated retention capacity and then liquid uptake rate values according to the procedures described herein. The results are described in Table 1.

Example 2

In Samples 9 through 16, absorbent structures are prepared comprising a superabsorbent material, a wettable staple fiber and a wettable binder fiber. For the superabsorbent material, a poly(acrylic acid) high-absorbency material, commercially available from Hoechst Celanese under the trade name designation IN 5000P, is used. For the wettable staple fiber, a wood pulp fluff is used. For the wettable binder fiber, a hydrophilic nylon-6, polyethylene oxide diamine blockcopolymer, which is commercially available from Allied-Signal, Inc. under the trade name designation HYDROFIL™, is used.

The wettable binder fiber was meltblown into an entangled composite web with the superabsorbent material fed into the meltblown stream and the staple fiber fed into the composite web structure with a picker roll. The absolute and relative basis weight amounts used of the different materials for Samples 9 through 16 is indicated in Table 2. The basis weight amounts are given in grams per square meter (g/sm) of absorbent composition formed. The samples are evaluated for liquid saturated retention capacity and then liquid uptake rate values according to the procedures described herein. The results are described in Table 2.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

TABLE 1

| Sample No. | Binder Fiber Basis Wt. | | Super-absorbent Basis Wt. | | Staple Fiber Basis Wt. | | Total Basis | Absolute Liquid Saturated Retention | Liquid Uptake Rate (mls/sec) | | |
|---|---|---|---|---|---|---|---|---|---|---|---|
| | (g/sm) | % | (g/sm) | % | (g/sm) | % | (g/sm) | Capacity (ml) | Insult 1 | Insult 2 | Insult 3 |
| 1* | 110 | 24 | 350 | 76 | 0 | 0 | 460 | 189 | 2.0 | 1.0 | 0.5 |
| 2 | 99 | 21 | 321 | 68 | 52 | 11 | 472 | 194 | 5.0 | 6.5 | 4.0 |
| 3 | 106 | 21 | 342 | 68 | 55 | 11 | 503 | 172 | 5.5 | 5.5 | 2.0 |
| 4* | 107 | 25 | 321 | 75 | 0 | 0 | 428 | 155 | — | — | 0.49 |
| 5 | 70 | 12.5 | 420 | 75 | 70 | 12.5 | 560 | 231 | — | — | 6.84 |
| 6* | 158 | 25 | 472 | 75 | 0 | 0 | 630 | 230 | 10 | 5 | 1.2 |
| 7 | 64 | 10 | 476 | 75 | 95 | 15 | 635 | 249 | 11 | 7.1 | 2.6 |
| 8 | 77 | 10 | 459 | 60 | 229 | 30 | 765 | 273 | 10.6 | 9.1 | 5.0 |

*Not an example of the present invention.

TABLE 2

| Sample No. | Binder Fiber Basis Wt. | | Super-absorbent Basis Wt. | | Staple Fiber Basis Wt. | | Total Basis | Absolute Liquid Saturated Retention | Liquid Uptake Rate (mls/sec) | | |
|---|---|---|---|---|---|---|---|---|---|---|---|
| | (g/sm) | % | (g/sm) | % | (g/sm) | % | (g/sm) | Capacity (ml) | Insult 1 | Insult 2 | Insult 3 |
| 9* | 150 | 50 | 150 | 50 | 0 | 0 | 300 | 100 | 1.3 | 0.47 | 0.16 |
| 10 | 120 | 40 | 150 | 50 | 30 | 10 | 30 | 131 | 2.5 | 1.55 | 0.6 |
| 11 | 60 | 20 | 150 | 50 | 90 | 30 | 300 | 134 | 3.2 | 3.0 | 1.3 |
| 12* | 200 | 70 | 85 | 30 | 0 | 0 | 285 | 77 | 1.9 | 0.8 | 0.29 |
| 13 | 114 | 40 | 85 | 30 | 86 | 30 | 285 | 95 | 2.75 | 2.5 | 0.73 |
| 14 | 100 | 35 | 85 | 30 | 100 | 35 | 285 | 94 | 4.27 | 2.0 | 1.3 |
| 15* | 200 | 80 | 50 | 20 | 0 | 0 | 250 | 61 | 2.0 | 1.1 | 0.57 |
| 16* | 160 | 64 | 50 | 20 | 40 | 16 | 250 | 69 | 2.2 | 0.58 | 0.75 |

*Not an example of the present invention.

What is claimed is:

1. An absorbent structure consisting essentially of:
   a. from about 25 to about 99 weight percent superabsorbent material wherein the superabsorbent material is capable of absorbing an amount of water at least about 10 times the weight of the superabsorbent material;
   b. from greater than 0 to about 35 weight percent wettable staple fiber, wherein the wettable staple fiber exhibits a length that is from about 0.2 centimeter to about 15 centimeters; and
   c. from greater than 0 to about 40 weight percent wettable binder fiber;

wherein all weight percents are based on the total weight of the superabsorbent material, wettable staple fiber, and wettable binder fiber in the absorbent structure, and wherein the absorbent structure exhibits a liquid uptake rate at least about 2 times greater than the liquid uptake rate exhibited by an otherwise substantially identical absorbent structure without any wettable staple fiber for any of three 60 milliliter insults of synthetic urine at about 23° C. applied at a rate of about 15 milliliters/second with about 5 minutes between each insult wherein the insults are applied to the absorbent structure with an absolute liquid saturated retention capacity of at least about 240 milliliters.

2. The absorbent structure of claim 1 comprising from about 65 to about 95 weight percent superabsorbent material.

3. The absorbent structure of claim 2 comprising from about 75 to about 90 weight percent superabsorbent material.

4. The absorbent structure of claim 1 comprising from about 1 to about 30 weight percent wettable staple fiber.

5. The absorbent structure of claim 4 comprising from about 5 to about 20 weight percent wettable staple fiber.

6. The absorbent structure of claim 1 comprising from about 1 to about 30 weight percent wettable binder fiber.

7. The absorbent structure of claim 6 comprising from about 5 to about 20 weight percent wettable binder fiber.

8. The absorbent structure of claim 1 exhibiting a liquid uptake rate at least about 5 times greater than the liquid uptake rate exhibited by an otherwise identical absorbent structure without any wettable staple fiber.

9. The absorbent structure of claim 8 exhibiting a liquid uptake rate at least about 10 times greater than the liquid uptake rate exhibited by an otherwise identical absorbent structure without any wettable staple fiber.

10. The absorbent structure of claim 1 comprising a fibrous matrix comprising the wettable binder fiber, wherein the fibrous matrix constrains the wettable staple fiber and the superabsorbent material.

11. The absorbent structure of claim 10 comprising from about 65 to about 95 weight percent superabsorbent material, from about 1 to about 30 weight percent wettable staple fiber, and from about 1 to about 30 weight percent wettable binder fiber.

12. The absorbent structure of claim 1 wherein the superabsorbent material is a synthetic hydrogel material.

13. The absorbent structure of claim 12 wherein the synthetic hydrogel material is a polyacrylate material.

14. The absorbent structure of claim 1 wherein the wettable staple fiber has a fiber length from about 0.1 to about 15 centimeters.

15. The absorbent structure of claim 1 wherein the wettable staple fiber has a fiber length from about 0.2 to about 7 centimeters.

16. The absorbent structure of claim 1 wherein the wettable staple fiber is selected from the group consisting of cellulosic fibers, textile fibers, and synthetic polymeric fibers.

17. The absorbent structure of claim 1 wherein the wettable binder fiber is a meltblown fiber formed from a hydrophilic nylon copolymer material.

18. The absorbent structure of claim 1 wherein the absorbent structure exhibits a liquid uptake rate at least about 2 times greater than the liquid uptake rate exhibited by an otherwise identical absorbent structure without any wettable staple fiber for the third of three 60 milliliter insults.

19. The absorbent structure of claim 1 wherein the absorbent structure exhibits a liquid uptake rate at least about 2 times greater than the liquid uptake rate exhibited by an otherwise identical absorbent structure without any wettable staple fiber for each of three 60 milliliter insults.

20. An absorbent structure consisting essentially of:
   a. from about 65 to about 95 weight percent synthetic hydrogel material wherein the synthetic hydrogel material is capable of absorbing an amount of water at least about 10 times the weight of the synthetic hydrogel material;
   b. from about 1 to about 30 weight percent wettable staple fiber, wherein the wettable staple fiber exhibits a length that is from about 0.2 centimeter to about 15 centimeters; and
   c. from about 1 to about 30 weight percent wettable finder fiber;
wherein all weight percents are based on the total weight of the synthetic hydrogel material, wettable staple fiber, and wettable binder fiber in the absorbent structure, and wherein the absorbent structure exhibits a liquid uptake rate at least about 2.5 times greater than the liquid uptake rate exhibited by an otherwise substantially identical absorbent structure without any wettable staple fiber for the third of three 60 milliliter insults of synthetic urine at about 23° C. applied at a rate of about 15 milliliters/second with about 5 minutes between each insult wherein the insults are applied to the absorbent structure with an absolute liquid saturated retention capacity of at least about 240 milliliters.

21. A disposable garment comprising:
   a bodyside liner, an outer cover, and an absorbent structure positioned between the bodyside liner and the outer cover, wherein the absorbent structure consists essentially of:
   a. from about 25 to about 99 weight percent superabsorbent material wherein the superabsorbent material is capable of absorbing an amount of water at least about 10 times the weight of the superabsorbent material;
   b. from greater than 0 to about 35 weight percent wettable staple fiber, wherein the wettable staple fiber exhibits a length that is from about 0.2 centimeter to about 15 centimeters; and
   c. from greater than 0 to about 40 weight percent binder fiber;
wherein all weight percents are based on the total weight of the superabsorbent material, wettable staple fiber, and wettable binder fiber in the absorbent structure, and wherein the absorbent structure exhibits a liquid uptake rate at least 2 times greater than the liquid uptake rate exhibited by an otherwise substantially identical absorbent structure without any wettable staple fiber for any of three 60 milliliter insults of synthetic urine at about 23° C. applied at a rate of about 15 milliliters/second with 5 minutes between each insult, wherein the insults are applied to the absorbent structure with an absolute liquid saturated retention capacity of at least about 240 milliliters.

22. The disposable absorbent garment of claim 21 wherein the absorbent structure comprises from about 65 to about 95 weight percent superabsorbent material.

23. The disposable absorbent garment of claim 22 wherein the absorbent structure comprises from about 75 to about 90 weight percent superabsorbent material.

24. The disposable absorbent garment of claim 21 wherein the absorbent structure comprises from about 1 to about 30 weight percent wettable staple fiber.

25. The disposable absorbent garment of claim 24 wherein the absorbent structure comprises from about 5 to about 20 weight percent wettable staple fiber.

26. The disposable absorbent garment of claim 21 wherein the absorbent structure comprises from about 1 to about 30 weight percent wettable binder fiber.

27. The disposable absorbent garment of claim 26 wherein the absorbent structure comprises from about 5 to about 20 weight percent wettable binder fiber.

28. The disposable absorbent garment of claim 21 wherein the absorbent structure exhibits a liquid uptake rate at least about 5 times greater than the liquid uptake rate exhibited by an otherwise identical absorbent structure without any wettable staple fiber.

29. The disposable absorbent garment of claim 28 wherein the absorbent structure exhibits a liquid uptake rate at least about 10 times greater than the liquid uptake rate exhibited by an otherwise identical absorbent structure without any wettable staple fiber.

30. The disposable absorbent garment of claim 21 wherein the absorbent structure comprises a fibrous matrix comprising the wettable binder fiber wherein the fibrous matrix constrains the wettable staple fiber and the superabsorbent material.

31. The disposable absorbent garment of claim 30 wherein the absorbent structure comprises from about 65 to about 95 weight percent superabsorbent material, from about 1 to about 30 weight percent wettable staple fiber, and from about 1 to about 30 weight percent wettable binder fiber.

32. The disposable absorbent garment of claim 21 wherein the superabsorbent material is a synthetic hydrogel material.

33. The disposable absorbent garment of claim 32 wherein the synthetic hydrogel material is a polyacrylate material.

34. The disposable absorbent garment of claim 21 wherein the wettable staple fiber has a fiber length from about 0.1 to about 15 centimeters.

35. The disposable absorbent garment of claim 21 wherein the wettable staple fiber has a fiber length from about 0.2 to about 7 centimeters.

36. The disposable absorbent garment of claim 21 wherein the wettable staple fiber is selected from the group consisting of cellulosic fibers, textile fibers, and synthetic polymeric fibers.

37. The disposable absorbent garment of claim 21 wherein the wettable binder fiber is a meltblown fiber formed from a hydrophilic nylon copolymer material.

38. The disposable absorbent garment of claim 21 wherein the absorbent structure exhibits a liquid uptake rate at least about 2 times greater than the liquid uptake rate exhibited by an otherwise identical absorbent structure without any wettable staple fiber for the third of three 60 milliliter insults.

39. The disposable absorbent garment of claim 21 wherein the absorbent structure exhibits a liquid uptake rate at least about 2 times greater than the liquid uptake rate exhibited by an otherwise identical absorbent structure without any wettable staple fiber for each of three 60 milliliter insults.

* * * * *